US011130001B2

(12) United States Patent
Hong et al.

(10) Patent No.: US 11,130,001 B2
(45) Date of Patent: Sep. 28, 2021

(54) DISPLAY APPARATUS INCLUDING A LENS

(71) Applicant: Samsung Display Co., LTD., Yongin (KR)

(72) Inventors: Jong-Ho Hong, Seongnam-si (KR); Seung-Chan Lee, Suwon-si (KR); Won-Sang Park, Yongin-si (KR); Jong-In Baek, Suwon-si (KR)

(73) Assignee: Samsung Display Co., Ltd.

( * ) Notice: Subject to any disclaimer, the term of this patent is extended or adjusted under 35 U.S.C. 154(b) by 248 days.

(21) Appl. No.: 14/302,280

(22) Filed: Jun. 11, 2014

(65) Prior Publication Data
US 2015/0039061 A1 Feb. 5, 2015

(30) Foreign Application Priority Data
Jul. 30, 2013 (KR) .................. 10-2013-0090124

(51) Int. Cl.
*A61N 5/06* (2006.01)

(52) U.S. Cl.
CPC .... *A61N 5/0616* (2013.01); *A61N 2005/0626* (2013.01); *A61N 2005/0662* (2013.01); *A61N 2005/0663* (2013.01)

(58) Field of Classification Search
None
See application file for complete search history.

(56) References Cited

U.S. PATENT DOCUMENTS

| | | | | |
|---|---|---|---|---|
| 5,047,847 A | * | 9/1991 | Toda ................. | A61B 1/05 348/345 |
| 5,526,146 A | * | 6/1996 | Goodman ............ | H04N 13/305 349/5 |
| 5,771,066 A | * | 6/1998 | Barnea ............... | H04N 13/0404 348/54 |
| 5,877,829 A | * | 3/1999 | Okamoto ............. | G02F 1/1323 349/110 |

(Continued)

FOREIGN PATENT DOCUMENTS

| KR | 1020070037834 A | 4/2007 |
|---|---|---|
| KR | 1020070043085 A | 4/2007 |

(Continued)

OTHER PUBLICATIONS

Lee et al.; "A Prospective, Randomized, Placebo-Controlled, Double-Blinded, and Split-Face Clinical Study on LED Phototherapy for Skin Rejuvenation: Clinical, Profilometric, Histologic, Ultrastructural, and Biochemical Evaluations and Comparison of Three Different Treatment Settings"; Science Direct, Journal of Photochemistry and Photobiology B: Biology 88 (2007) pp. 51-67.

(Continued)

*Primary Examiner* — Carl H Layno
*Assistant Examiner* — Manolis Pahakis
(74) *Attorney, Agent, or Firm* — Innovation Counsel LLP

(57) ABSTRACT

A display apparatus providing light therapy includes a display panel configured to display an image to a display region based on input image data, and a lens part disposed on the display panel, the lens part configured to focus the (Continued)

image displayed by the display panel toward a first region in a therapy mode, in which the first region is smaller than the display region, and the first region may correspond to a position of a user's face.

8 Claims, 9 Drawing Sheets

(56) References Cited

U.S. PATENT DOCUMENTS

| | | | |
|---|---|---|---|
| 6,859,333 B1* | 2/2005 | Ren | G02B 3/14 359/666 |
| 6,943,754 B2* | 9/2005 | Aughey | A61B 3/113 345/7 |
| 7,248,271 B2* | 7/2007 | Credelle | G09G 3/3607 345/694 |
| 7,400,377 B2* | 7/2008 | Evans | G02F 1/1323 349/194 |
| 7,551,239 B2* | 6/2009 | Fukushima | G02F 1/1323 349/16 |
| 7,782,382 B2* | 8/2010 | Fujimura | H04N 5/23293 345/4 |
| 8,314,918 B2* | 11/2012 | Kean | G02F 1/1323 349/123 |
| 8,525,754 B2* | 9/2013 | Sumiyoshi | G09G 5/00 345/4 |
| 8,558,853 B2* | 10/2013 | Sagardoyburu | G02B 27/0093 345/690 |
| 8,629,821 B2* | 1/2014 | Borgers | G09G 3/3648 345/204 |
| 8,896,507 B2* | 11/2014 | Broughton | G02F 1/1323 345/84 |
| 8,956,396 B1* | 2/2015 | Friend | A61N 5/06 607/88 |
| 9,030,534 B2* | 5/2015 | Cha | H04N 13/366 348/51 |
| 9,250,655 B2* | 2/2016 | Davis | G06F 1/1616 |
| 9,285,883 B2* | 3/2016 | Bi | G06F 1/1694 |
| 9,348,160 B2* | 5/2016 | Hsu | G02F 1/1323 |
| 2003/0036750 A1* | 2/2003 | Ruiz | G03F 7/70291 606/5 |
| 2004/0021802 A1* | 2/2004 | Yoshino | C08F 4/642 349/1 |
| 2005/0083246 A1* | 4/2005 | Saishu | H04N 13/317 345/1.1 |
| 2005/0237622 A1* | 10/2005 | Yoshino | G02B 30/54 359/618 |
| 2005/0243265 A1* | 11/2005 | Winlow | G02F 1/1323 349/178 |
| 2006/0020309 A1* | 1/2006 | Altshuler | A61B 18/203 607/88 |
| 2006/0050016 A1* | 3/2006 | Tomisawa | G02B 30/27 345/32 |
| 2007/0035672 A1* | 2/2007 | Shestak | H04N 13/359 349/15 |
| 2007/0097287 A1* | 5/2007 | Kim | G02F 1/29 349/61 |
| 2007/0109400 A1* | 5/2007 | Woodgate | G02B 30/27 348/47 |
| 2007/0126669 A1* | 6/2007 | Seto | G02B 27/0093 345/76 |
| 2007/0188667 A1* | 8/2007 | Schwerdtner | G02B 30/26 349/15 |
| 2007/0268234 A1* | 11/2007 | Wakabayashi | A61M 21/00 345/102 |
| 2008/0117153 A1 | 5/2008 | Fujine et al. | |
| 2008/0275533 A1* | 11/2008 | Powell | A61N 5/0616 607/88 |
| 2009/0180180 A1* | 7/2009 | Shimshi | G02B 27/2214 359/462 |
| 2009/0213147 A1* | 8/2009 | Sagardoyburu | G06F 1/3231 345/690 |
| 2009/0244682 A1* | 10/2009 | Saishu | H04N 13/307 359/246 |
| 2009/0281604 A1* | 11/2009 | De Boer | A61M 21/00 607/88 |
| 2009/0326616 A1* | 12/2009 | Aarts | A61B 5/486 607/88 |
| 2010/0026920 A1* | 2/2010 | Kim | H04N 13/305 349/15 |
| 2010/0076527 A1* | 3/2010 | Hammond | G09F 9/33 607/88 |
| 2010/0082081 A1* | 4/2010 | Niessen | A61N 5/0601 607/88 |
| 2010/0149073 A1* | 6/2010 | Chaum | G02B 27/0172 345/8 |
| 2010/0171441 A1* | 7/2010 | Schlangen | A61M 21/00 315/294 |
| 2010/0208163 A1* | 8/2010 | Fuchikami | G02B 27/0093 349/62 |
| 2010/0264850 A1* | 10/2010 | Yamamoto | G09G 5/14 315/312 |
| 2010/0302468 A1* | 12/2010 | Lin | G02F 1/1347 349/15 |
| 2010/0328438 A1* | 12/2010 | Ohyama | H04N 13/361 348/51 |
| 2011/0069254 A1* | 3/2011 | Takama | G02B 3/14 349/62 |
| 2011/0085094 A1* | 4/2011 | Kao | G02B 30/27 349/5 |
| 2011/0184498 A1* | 7/2011 | Donley | A61B 3/0041 607/88 |
| 2011/0199548 A1* | 8/2011 | Takama | G02F 1/29 349/15 |
| 2011/0205342 A1* | 8/2011 | Lin | H04N 13/359 348/54 |
| 2011/0304612 A1* | 12/2011 | Ohyama | G02B 30/27 345/419 |
| 2011/0316881 A1* | 12/2011 | Yoshifuji | H04N 13/31 345/634 |
| 2012/0092586 A1* | 4/2012 | He | G02B 30/27 349/61 |
| 2012/0130455 A1 | 5/2012 | Baird et al. | |
| 2012/0154270 A1* | 6/2012 | Numao | H04N 5/72 345/156 |
| 2012/0218325 A1* | 8/2012 | Hiroki | G09G 3/003 345/697 |
| 2012/0242913 A1* | 9/2012 | Miyazawa | G02B 30/27 349/5 |
| 2012/0250141 A1* | 10/2012 | Chen | G02F 1/29 359/320 |
| 2012/0257018 A1* | 10/2012 | Shigemura | G02B 30/27 348/46 |
| 2012/0257127 A1* | 10/2012 | Miyazawa | H04N 13/305 349/15 |
| 2012/0259392 A1* | 10/2012 | Feng | A61N 5/0618 607/88 |
| 2012/0307169 A1* | 12/2012 | Ohyama | G02F 1/29 349/33 |
| 2012/0320288 A1* | 12/2012 | Baek | H04N 13/359 349/5 |
| 2013/0002970 A1* | 1/2013 | Baek | G02F 1/29 349/5 |
| 2013/0027772 A1* | 1/2013 | Large | G02B 27/0075 359/464 |
| 2013/0076723 A1* | 3/2013 | Niioka | G02F 1/1362 345/212 |
| 2013/0127831 A1* | 5/2013 | Kim | H04N 13/31 345/419 |
| 2013/0190845 A1* | 7/2013 | Liu | A61N 5/0616 607/90 |
| 2013/0201415 A1* | 8/2013 | Chang | G02F 1/29 349/15 |
| 2013/0215364 A1* | 8/2013 | Huang | G02B 27/0093 349/69 |
| 2013/0218240 A1* | 8/2013 | Feng | A61N 5/0618 607/90 |

(56) References Cited

U.S. PATENT DOCUMENTS

| | | | |
|---|---|---|---|
| 2013/0235304 A1* | 9/2013 | Lee | G02F 1/29 349/96 |
| 2013/0238060 A1* | 9/2013 | Nevins | A61N 5/0613 607/90 |
| 2013/0265227 A1* | 10/2013 | Julian | G06F 3/04812 345/157 |
| 2013/0314581 A1* | 11/2013 | Kido | H04N 5/23219 348/333.12 |
| 2014/0016051 A1* | 1/2014 | Kroll | G02B 30/26 349/15 |
| 2014/0058483 A1* | 2/2014 | Zao | A61N 5/06 607/88 |
| 2014/0128941 A1* | 5/2014 | Williams | A61N 5/06 607/88 |
| 2014/0240303 A1* | 8/2014 | Chiang | G09G 3/3696 345/212 |
| 2014/0267284 A1* | 9/2014 | Blanche | H04N 13/0402 345/428 |
| 2014/0285643 A1* | 9/2014 | Usukura | H04N 13/144 348/59 |
| 2014/0292732 A1* | 10/2014 | Niioka | G02F 1/134363 345/204 |
| 2015/0049176 A1* | 2/2015 | Hinnen | H04N 13/305 348/59 |
| 2015/0051672 A1* | 2/2015 | Jo | A61N 5/06 607/90 |
| 2015/0130751 A1* | 5/2015 | Teraguchi | G06F 3/0412 345/174 |
| 2015/0228226 A1* | 8/2015 | Luebke | G09G 3/3406 345/690 |
| 2015/0283399 A1* | 10/2015 | Guglielmi | G02B 19/0066 604/20 |
| 2016/0124239 A1* | 5/2016 | Kim | B05D 3/12 349/194 |
| 2016/0270656 A1* | 9/2016 | Samec | A61B 3/1035 |

FOREIGN PATENT DOCUMENTS

| | | |
|---|---|---|
| KR | 1020070043088 A | 4/2007 |
| KR | 1020070045382 A | 5/2007 |
| KR | 1020070046247 A | 5/2007 |
| KR | 10-2007-0116937 A | 12/2007 |
| KR | 1020110015976 A | 2/2011 |
| KR | 10-2012-0069133 A | 6/2012 |
| KR | 1020120095217 A | 8/2012 |

OTHER PUBLICATIONS

Barolet; "Light-Emitting Diodes (LEDs) in Dermatology"; Elsevier Inc., Seminars in Cutaneous Medicine and Surgery; (2008.); pp. 227-238.

Korean Office Action corresponding to Korean Patent Application No. 10-2013-0090124 dated Jul. 31, 2019 6 pages.

* cited by examiner 100  200

DISPLAY APPARATUS INCLUDING A LENS

PRIORITY STATEMENT

This application claims priority under 35 U.S.C. § 119 to Korean Patent Application No. 10-2013-0090124, filed on Jul. 30, 2013 in the Korean Intellectual Property Office KIPO, the contents of which are herein incorporated by reference in their entireties.

BACKGROUND OF THE INVENTION

1. Field of the Invention

The disclosure relates to a light therapy display apparatus. More particularly, example embodiments of the present invention relate to a light therapy display apparatus providing a skin treatment effect and a skin therapy effect.

2. Description of the Related Art

The amount of time that display apparatuses such as televisions, monitors, smartphones, laptop computers and tablet PCs are used by contemporary people has been increasing. A conventional display apparatus merely provides audio and visual information to a user.

According to recent studies, certain light may positively affect a human skin. When a blue light, a green light and a red line among visible lights are emitted to the skin, acne may be cured, the skin may be whitened and/or a wrinkle may be improved. The above-mentioned skin treatment effect and the skin therapy effect using the light may be referred to as a light therapy.

For the skin treatment and the skin therapy, people may go to a skin care center or may buy a light therapy apparatus for family use.

BRIEF SUMMARY OF THE INVENTION

A display apparatus providing a light therapy is provided.

A display apparatus a display panel configured to display an image to a display region based on input image data; and a lens part disposed on the display panel, the lens part configured to focus the image displayed by the display panel toward a first region in a therapy mode, in which the first region is smaller than the display region.

The display panel may use a first color coordinate in a display mode and a second color coordinate in the therapy mode.

A wavelength of blue light may be about 415 nm in the second color coordinate. A wavelength of green light may be about 550 nm in the second color coordinate. A wavelength of red light may be about 633 nm in the second color coordinate.

The display apparatus may further include a display panel driver driving the display panel and a lens driver driving the lens part. The display panel driver may include a therapy controlling part configured to output first image data in a display mode and second image data in the therapy mode. The therapy controlling part may be configured to output a lens driving signal to the lens driver in the therapy mode.

The display apparatus may further include a user detecting configured to determine a position of an object relative to the lens part.

The lens part may adjust a position of the first region to correspond to the position of the object.

The user detecting part may be configured to determine a distance of an object from the lens part. A focal length of the lens part may be adjusted based on the distance of the object.

The user detecting part may be configured to determine a distance of an object from the lens part. Intensity of the image of the display panel may be adjusted based on the distance.

The object may be a human face, and the user detecting part may be configured to determine distances of portions of the human face from the lens part. Focal lengths of the lens units may be adjusted based on the distances of the portions of the human's face.

The object may be a human face and user detecting part may be configured to determine a skin condition of the human face. The lens part may include a plurality of lens units. The lens units of the lens part may focus lights having different wavelengths to different regions each corresponding to a position of different portions of the human face according to the skin condition of the human face.

The lens part may include a liquid crystal lens.

The display panel and the lens part may have curved shapes.

In another aspect, a display apparatus providing light therapy includes a display panel. The display panel is configured to display a first image based on input image data in a display mode. The display panel is configured to display a second image having a therapy wavelength in a therapy mode.

The therapy wavelength may be one of about 415 nm representing blue, about 550 nm representing green and about 633 nm representing red.

The display apparatus may further include a user detecting part configured to determine a position of an object relative to the display panel.

The user detecting part may be configured to determine a distance of the object from the display panel. Intensity of the second image may be adjusted based on the distance.

The display apparatus may further include a display panel driver driving the display panel. The display panel driver may include a therapy controlling part configured to manage the therapy wavelength, duration of therapy and the intensity of the second image based on the distance.

The object may be a human face and therapy controlling part may be configured to compare a skin condition of the human face before therapy and a skin condition of the human face after therapy using the user detecting part and to provide a comparison result to the display panel.

According to the light therapy display apparatus, an image is focused on a user's face or a therapy image is displayed on a display panel in a therapy mode. Thus, the display apparatus may provide the skin care effect and the skin therapy effect.

BRIEF DESCRIPTION OF THE DRAWINGS

The above and other features and advantages will become more apparent by describing in detailed example embodiments thereof with reference to the accompanying drawings, in which.

DETAILED DESCRIPTION OF THE INVENTION

Hereinafter, example embodiments will be described in further detail with reference to the accompanying drawings.

Figure 1:
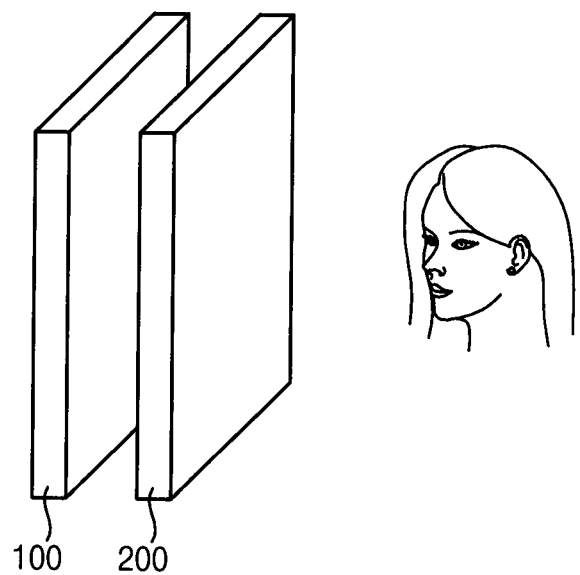
FIG. 1 is a perspective view illustrating a display apparatus according to an example embodiment.
Figure 2A:
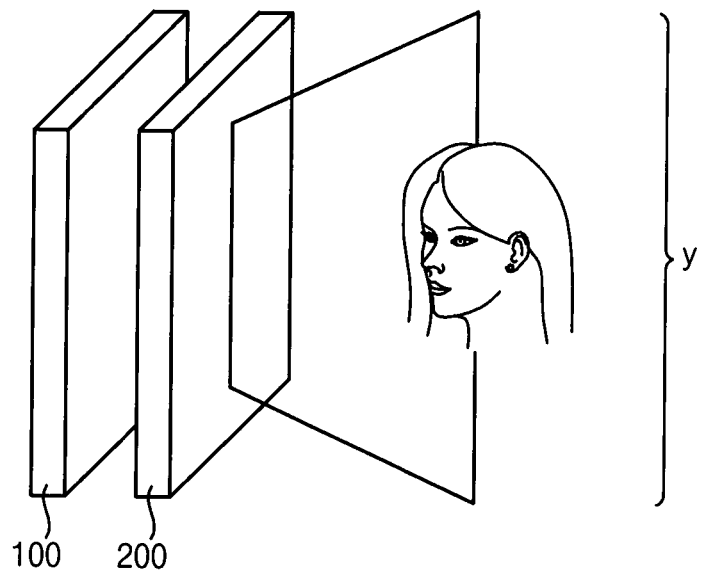
FIG. 2A is a perspective view illustrating an angle of an image displayed by the display apparatus of FIG. 1 in a display mode.
Figure 2B:
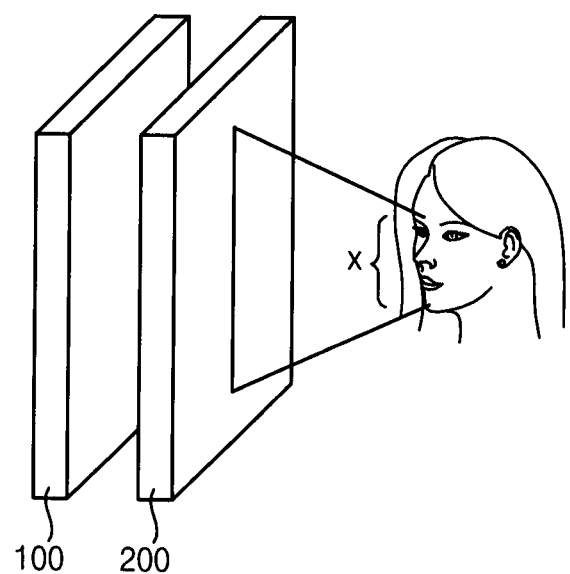
FIG. 2B is a perspective view illustrating an angle of an image displayed by the display apparatus of FIG. 1 in a therapy mode.

FIG. 1 is a perspective view illustrating a display apparatus according to an example embodiment. FIG. 2A is a perspective view illustrating an angle of an image displayed by the display apparatus of FIG. 1 in a display mode. FIG. 2B is a perspective view illustrating an angle of an image displayed by the display apparatus of FIG. 1 in a therapy mode.

Referring to FIGS. 1, 2A and 2B, the display apparatus includes a display panel 100 and a lens part 200.

In the present example embodiment, the display apparatus may be one of a television, a monitor, a smartphone, a PDP, a laptop computer, a tablet PC.

The display panel 100 displays an image based on input image data.

The lens part 200 is disposed on the display panel 100. In a display mode, the lens part 200 transmits the image of the display panel 100 without refraction. In a therapy mode, the lens part 200 focuses, or concentrates, the image of the display panel 100 toward a user's face.

For example, the lens part 200 may be a liquid crystal lens using a refractive index of a liquid crystal molecule. Alternatively, the lens part 200 may be a liquid lens using electro-wetting, or the lens part 200 may be a Fresnel lens including a plurality of lens parts forming a single lens.

As an alternative to what is shown in FIG. 1, the lens part 200 may be formed so that it is integrated with the display panel 100. For example, the lens part 200 may be formed in a pixel part of the display panel 100.

As shown in FIG. 2A, the display apparatus displays an image having a relatively wide viewing angle in the display mode. As shown in FIG. 2A, a display region [y] of an image display in the display mode is larger than an area occupied by a user's face. In the display mode, the lens part 200 transmits the image of the display panel 100 without refraction. In the display mode, the lens part 200 may be turned off.

As shown in FIG. 2B, the display apparatus displays an image having a relatively narrow viewing angle in the therapy mode. In the therapy mode, the lens part 200 focuses, or concentrates, the image of the display panel 100 toward the user's face. That is, the lens part 200 causes light emitted from the display panel 100 to be directed toward and converge on a particular region [x], and that particular region [x] may have a size and shape corresponding to a size and shape of a human user's face or portion of a user's face. The area of region [x] in particular is smaller than the display region [y] showing FIG. 2A. As used herein, the term "user's face" refers to the region [x] that is smaller than display region [y] and may have the size and shape of a user's face or portion thereof.

Thus, light having a relatively greater intensity may be emitted directly toward the user's skin. Therefore, the skin therapy such as acne removal, pain relief, skin reproduction, anti-wrinkle, whitening, and/or scar removal may be operated on the user's skin according to wavelengths of the image of the display panel 100.

Figure 3:
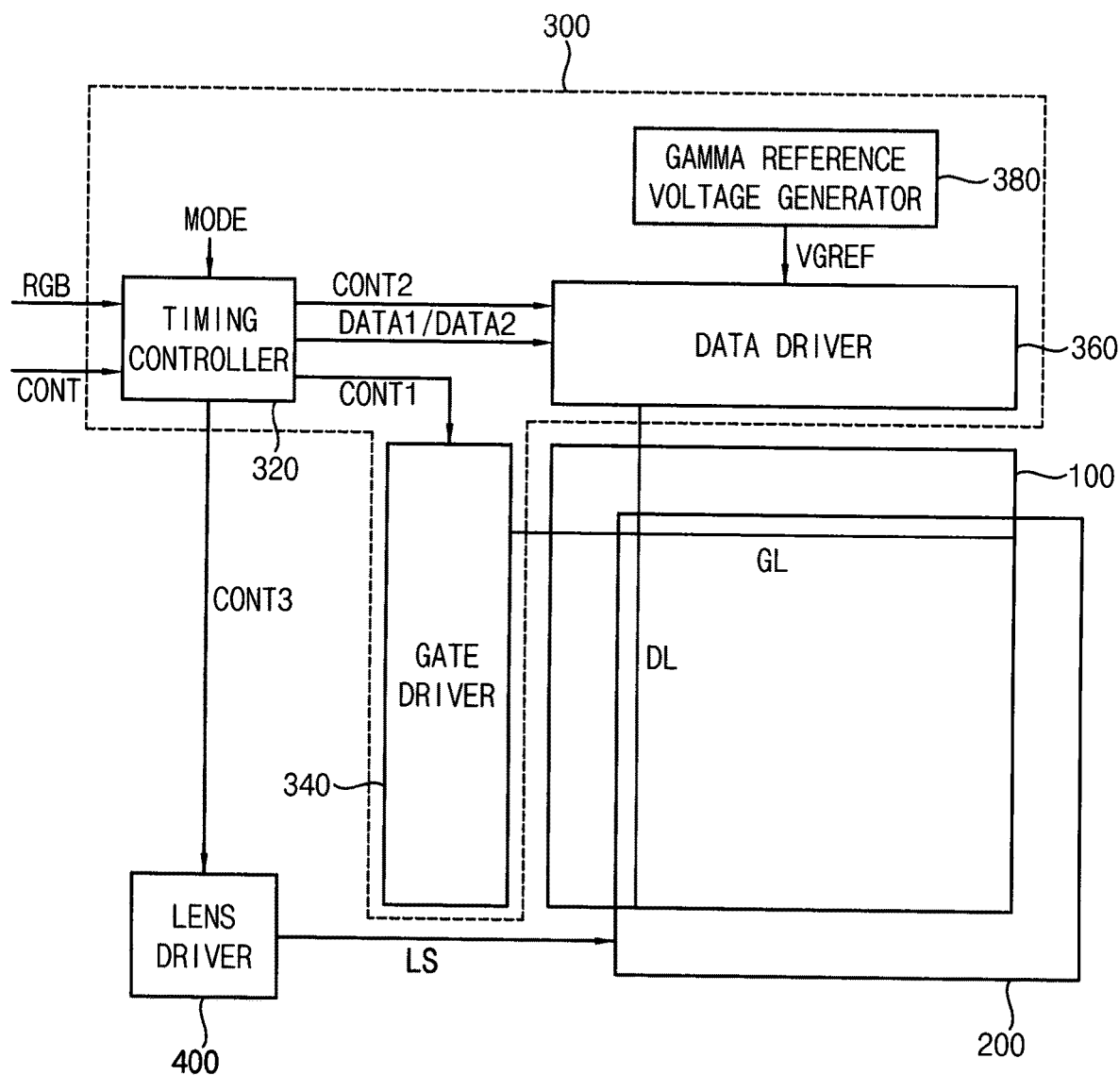
FIG. 3 is a block diagram illustrating the display apparatus of FIG. 1.

FIG. 3 is a block diagram illustrating the display apparatus of FIG. 1.

Referring to FIGS. 1 to 3, the display apparatus includes the display panel 100, the lens part 200, a display panel driver 300 and a lens driver 400.

The display panel 100 displays the image based on the input image data RGB. The display panel 100 includes a first substrate, a second substrate facing the first substrate and a liquid crystal layer (not shown) disposed between the first and second substrates.

The display panel 100 includes a plurality of pixels. The pixels may include, for example, a red subpixel, a green subpixel and a blue subpixel.

The display panel 100 includes a plurality of gate lines GL and a plurality of data lines DL. The subpixels are connected to the gate lines GL and the data lines DL. The gate lines GL extend in a first direction D1. The date lines DL extend in a second direction D2 crossing the first direction D1.

Each subpixel includes (not shown) a switching element and a liquid crystal capacitor electrically connected to the switching element. The subpixel may further include a storage capacitor. The subpixels are disposed in a matrix form. The switching element may be a thin film transistor.

The gate lines GL, the data lines DL, pixel electrodes and storage electrodes may be disposed on the first substrate. A common electrode may be disposed on the second substrate.

The lens part 200 is disposed on the display panel 100. In the display mode, the lens part 200 transmits the image of the display panel 100 without refraction. In the therapy mode, the lens part 200 refracts the image of the display panel 100 toward the user's face.

For example, the lens part 200 may include a third substrate, a fourth substrate facing the third substrate and a liquid crystal layer disposed between the third and fourth substrates.

The display panel driver 300 is connected to the display panel 100 to drive the display panel 100. The display panel driver 300 includes a timing controller 320, a gate driver 340, a data driver 360 and a gamma reference voltage generator 380.

The timing controller 320 receives the input image data RGB and an input control signal CONT from an external apparatus. The input image data RGB may include red image data R, green image data G and blue image data B. The input control signal CONT may include a master clock signal, a data enable signal, a vertical synchronizing signal and a horizontal synchronizing signal.

The timing controller 320 receives a mode signal MODE. The mode signal MODE represents one of the display mode and the therapy mode.

The timing controller 320 generates a first control signal CONT1, a second control signal CONT2, a third control signal CONT3, a first data signal DATA1 and a second data signal DATA2 based on the input image data RGB, the input control signal CONT and the mode signal MODE.

The timing controller 320 generates the first control signal CONT1 to control a driving timing of the gate driver 340 based on the input control signal CONT, and outputs the first control signal CONT1 to the gate driver 340. The first control signal CONT1 may include a vertical start signal and a gate clock signal.

The timing controller 320 generates the second control signal CONT2 to control a driving timing of the data driver 360 based on the input control signal CONT, and outputs the second control signal CONT2 to the data driver 360. The second control signal CONT2 may include a horizontal start signal and a load signal.

The timing controller 320 generates the first data signal DATA1 based on the input image data RGB, and outputs the first data signal DATA1 to the data driver 360 in the display mode. The first data signal DATA1 may be generated using a first color coordinate.

The timing controller 320 generates the second data signal DATA2 based on the input image data RGB, and outputs the second data signal DATA2 to the data driver 360 in the therapy mode. The second data signal DATA2 may be generated using a second color coordinate.

In the second color coordinate, for example, a wavelength of a blue light may be between about 385 nm and about 445 nm. A wavelength of a green light may be, for example, between about 520 nm and about 580 nm in the second color coordinate. A wavelength of a red light may be, for example, between about 603 nm and about 663 nm in the second color coordinate.

For example, the wavelength of the blue light may be about 415 nm in the second color coordinate, the wavelength of the green light may be about 550 nm in the second color coordinate, and the wavelength of the red light may be about 633 nm in the second color coordinate. The blue light having the wavelength of about 415 nm may have acne removal effect and pain relief effect. The green light having the wavelength of about 550 nm may have skin reproduction effect and anti-wrinkle effect. The red light having the wavelength of about 533 nm may have cell reproduction effect, anti-wrinkle effect, whitening effect, moisturizing effect and scar removal effect.

The second data signal DATA2 of the therapy mode may be substantially the same as the first data signal DATA1 of the display mode except that the second color coordinate is applied to the second data signal DATA2. Thus, the user may get the skin care effect and the skin therapy effect by using the television, the monitor and the smartphone in an ordinary way.

Alternatively, the second data signal DATA2 of the therapy mode may represent a therapy image not based on the input image data RGB. For example, the therapy image may display a single color image which has a wavelength having the skin care effect and the skin therapy effect.

The timing controller 320 may generate the first and second data signals DATA1 and DATA2 using the same color coordinate. For example, the timing controller 320 may generate the first and second data signals DATA1 and DATA2 using the second color coordinate having the skin therapy effect.

The timing controller 320 outputs the third control signal CONT3 to the lens driver 400 in the therapy mode. The third control signal CONT3 may be a lens control signal.

The gate driver 340 receives the first control signal CONT1 from the timing controller 320. The gate driver 340 generates gate signals for driving the gate lines GL in response to the first control signal CONT1. The gate driver 340 sequentially outputs the gate signals to the gate lines GL.

The gamma reference voltage generator 380 generates a gamma reference voltage VGREF. The gamma reference voltage generator 380 provides the gamma reference voltage VGREF to the data driver 360. The gamma reference voltages VGREF have values corresponding to the data signal DATA1 and DATA2. The gamma reference voltage generator 380 may be disposed in the data driver 360.

The data driver 360 receives the second control signal CONT2 and the data signal DATA1 and DATA2 from the timing controller 320. The data driver 360 receives the gamma reference voltage VGREF from the gamma reference voltage generator 380.

The data driver 360 converts the data signal DATA1 and DATA2 into data voltages having analog values using the gamma reference voltage VGREF. The data driver 360 outputs the data voltages to the data lines DL.

The lens driver 400 is connected to the lens part 200 to drive the lens part 200.

The lens driver 400 receives the third control signal CONT3 from the timing controller 320. The lens driver 400 generates a lens driving signal LS for driving the lens part 200 in response to the third control signal CONT3. The lens driver 400 outputs the lens driving signal LS to the lens part 200.

Figure 4:
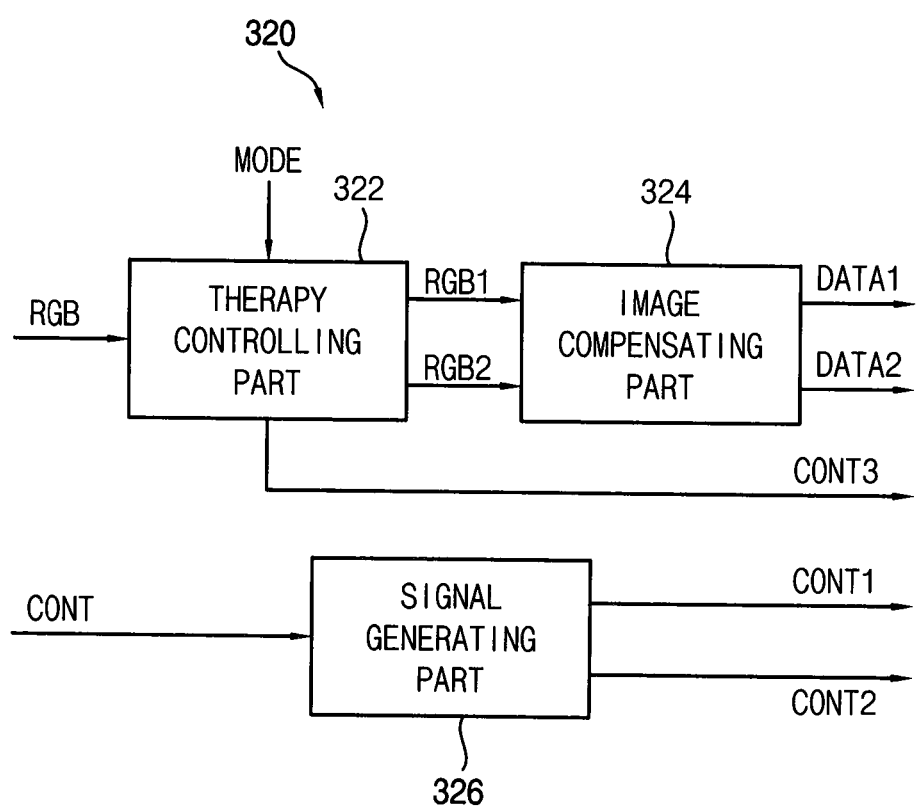
FIG. 4 is a block diagram illustrating a timing controller of FIG. 3.

FIG. 4 is a block diagram illustrating a timing controller of FIG. 3.

Referring to FIGS. 1 to 4, the timing controller 320 includes a therapy controlling part 322, an image compensating part 324 and a signal generating part 326. The timing controller 320 is logically divided into the above elements. The timing controller 320 may not be physically divided into the above elements.

The therapy controlling part 322 receives the input image data RGB and the mode signal MODE. The therapy controlling part 322 generates first image data RGB1 in the display mode and second image data RGB2 in the therapy mode.

The therapy controlling part 322 outputs the first and second image data RGB1 and RGB2 to the image compensating part 324. The therapy controlling part 322 outputs the third control signal CONT3 to the lens driver 400.

The image compensating part 324 receives the first and second image data RGB1 and RGB2 from the therapy controlling part 322.

The image compensating part 324 compensates a grayscale of the first and second image data RGB1 and RGB2. The image compensating part 324 may include, for example, an adaptive color correcting part (not shown) and a dynamic capacitance compensating part (not shown).

The adaptive color correcting part receives the grayscale data, and operates an adaptive color correction ("ACC"). The adaptive color correcting part may compensate the grayscale data using a gamma curve.

The dynamic capacitance compensating part operates a dynamic capacitance compensation ("DCC"), which compensates the grayscale data of present frame data using previous frame data and the present frame data.

The image compensating part 324 compensates the grayscale of the first and second image data RGB1 and RGB2, and rearranges the first and second image data RGB1 and RGB2 to generate first and second data signals DATA1 and DATA2 to correspond to a data type of the data driver 360. For instance, the first and second data signals DATA1 and DATA2 may have a digital type. The image compensating part 324 outputs the first and second data signals DATA1 and DATA2 to the data driver 360.

The signal generating part 326 receives the input control signal CONT. The signal generating part 326 generates the first control signal CONT1 to control a driving timing of the gate driver 320 based on the input control signal CONT. The signal generating part 326 generates the second control signal CONT2 to control a driving timing of the data driver 360 based on the input control signal CONT.

The signal generating part 326 outputs the first control signal CONT1 to the gate driver 320. The signal generating part 326 outputs the second control signal CONT2 to the data driver 360.

According to the present example embodiment, in the therapy mode, the display apparatus focuses, or concentrates, the image of the display panel 100 having the skin therapy effect toward the user's face using the lens part 200. Thus, when the user ordinarily uses the display apparatus to watch television, to communicate with others or to use an internet service, the display apparatus provides the skin care effect and the skin therapy effect to the user.

Figure 5:
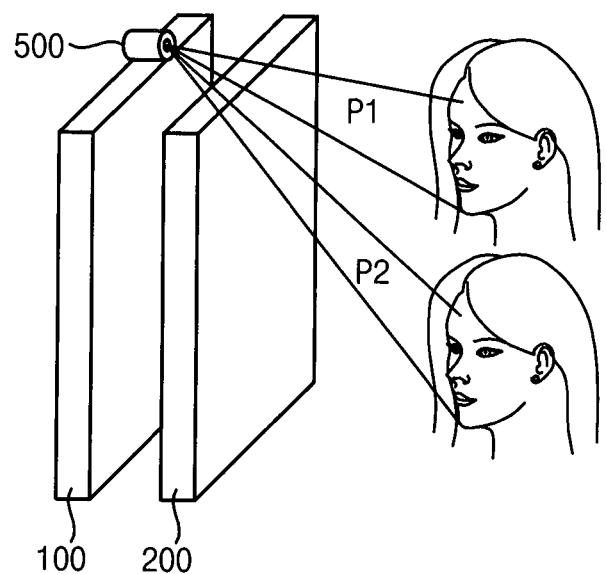
FIG. 5 is a perspective view illustrating a display apparatus according to an example embodiment.

FIG. 5 is a perspective view illustrating a display apparatus according to an example embodiment.

A display apparatus according to the present example embodiment is substantially the same as the display apparatus of the previous example embodiment explained referring to FIGS. 1 to 4 except that the display apparatus further includes a user detecting part. Thus, the same reference numerals will be used to refer to the same or like parts as those described in the previous example embodiment of FIGS. 1 to 4 and any repetitive explanation concerning the above elements will be omitted.

Referring to FIGS. 1 to 5, the display apparatus includes a display panel 100, a lens part 200 and the user detecting part 500.

The display panel 100 displays an image based on input image data.

The lens part 200 is disposed on the display panel 100. In a display mode, the lens part 200 transmits the image of the display panel 100 without refraction. In a therapy mode, the lens part 200 focuses the image of the display panel 100 toward a user's face.

The user detecting part 500 determines a position of an object relative to the display panel 100 and/or the lens part 200. The object may be, for example, a human face, for instance the face of a user of the display apparatus. For example, the user detecting part 500 may include a camera. For example, the user detecting part 500 may include a proximity sensor. For example, the user detecting part 500 may be disposed on a bezel portion of the display panel 100.

The user detecting part 500 may determine a position of an object, for instance, a user's face. The lens part 200 may concentrate the image of the display panel 100 toward the position identified as the position of the user's face. When the user's face is disposed at a first position P1, the lens part 200 focuses the image of the display panel 100 so that the light from the image of the display panel 100 is directed toward, and concentrated on, a position corresponding to the first position P1. When the user's face is disposed at a second position P2, the lens part 200 focuses the image of the display panel 100 so that the light from the image of the display panel 100 is directed toward, and concentrated on, a position corresponding to the second position P2.

For example, the user detecting part 500 transmits the position of the user's face to the therapy controlling part 322 of the timing controller 320. The therapy controlling part 322 outputs the different lens control signals to the lens driver 400, the lens control signal including the position information for the user's face. The lens driver 400 drives the lens part 200 to focus the image of the display panel 100 so that light from the image of the display panel 100 is directed toward, and concentrated on, the position of the user's face.

The user detecting part 500 may determine the position of the user's face in real-time. The lens part 200 may adjust a position where light from the image of the display panel 100 is focused in real-time.

According to the present example embodiment, the display apparatus focuses the image of the display panel 100 having the skin therapy effect so that light from the image of the display panel 100 is directed toward, and concentrated on, the position of a user's face using the lens part 200 in the therapy mode. Thus, when the user ordinarily uses the display apparatus to watch television, to communicate with others, or to use an internet service, the display apparatus provides the skin care effect and the skin therapy effect to the user.

In addition, the lens part 200 is adjusted according to the position of the user's face so that the skin care effect and the skin therapy effect may be further improved.

Figure 6:
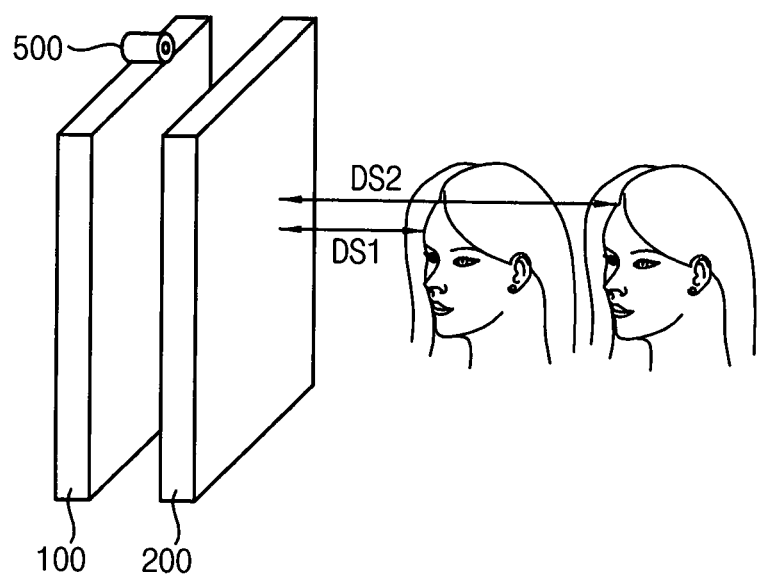
FIG. 6 is a perspective view illustrating a display apparatus according to an example embodiment.

FIG. 6 is a perspective view illustrating a display apparatus according to an example embodiment.

A display apparatus according to the present example embodiment is substantially the same as the display apparatus of the previous example embodiment explained referring to FIGS. 1 to 4 except that the display apparatus further includes a user detecting part. Thus, the same reference numerals will be used to refer to the same or like parts as those described in the previous example embodiment of FIGS. 1 to 4 and any repetitive explanation concerning the above elements will be omitted.

Referring to FIGS. 1 to 4 and 6, the display apparatus includes a display panel 100, a lens part 200 and the user detecting part 500.

The display panel 100 displays an image based on input image data.

The lens part 200 is disposed on the display panel 100. In a display mode, the lens part 200 transmits the image of the display panel 100 without refraction. In a therapy mode, the lens part 200 focuses the image of the display panel 100 toward a user's face.

The user detecting part 500 determines a distance of an object, for instance a human face of a user, from the lens part 200. Alternatively, the user detecting part 500 determines a distance of an object, for instance a human face of a user, from the display panel 100. The lens part 200 is disposed directly on the display panel 100 so that the distance of the object from the lens part may be substantially the same as the distance of the object from the display panel 100. For example, the user detecting part 500 may include a camera. For example, the user detecting part 500 may include a proximity sensor. For example, the user detecting part 500 may be disposed on a bezel portion of the display panel 100.

A focal length of the lens part 200 may be adjusted based on the distance of the user away from the lens part 200. When the user is disposed at a first distance DS1 from the lens part 200, the focal length of the lens part 200 is adjusted to focus the image of the display panel 100 so that light from the image of the display panel 100 is directed onto, and concentrated at, the position of the user at the first distance DS1. When the user is disposed at a second distance DS2 from the lens part 200, the focal length of the lens part 200 is adjusted to focus the image of the display panel 100 so that light from the image of the display panel 100 is directed onto, and concentrated at, the position of the user at the second distance DS2.

For example, the user detecting part 500 transmits the distance of the user to the therapy controlling part 322 of the timing controller 320. The therapy controlling part 322 outputs the different lens control signals to the lens driver 400 based on the distance of the user from the lens part 200. The lens driver 400 drives the lens part 200 to focus the light from the image of the display panel 100 so that light from the image of the display panel 100 is directed onto, and concentrated at, the position of the user at the distance measured.

In addition, intensity of the image of the display panel 100 may be adjusted based on the distance of the user from the lens part 200. When the user is relatively close to the lens part 200, the intensity of the image of the display panel 100 may be weakened. When the user is relatively far from the lens part 200, the intensity of the image of the display panel 100 may be strengthened.

For example, the user detecting part 500 transmits the distance of the user from the display panel 100 to the therapy controlling part 322 of the timing controller 320. The therapy controlling part 322 adjusts the intensity of the image of the display panel 100 based on the distance of the user from the lens part 200.

For example, the therapy controlling part 322 may manage a wavelength of the image of the display panel 100, duration of the therapy, and the intensity of the image of the display panel 100 according to the distance of the user. The wavelength of the image of the display panel 100 and the duration of the therapy may be fixed values. The intensity of the image of the display panel 100 may be a variable based on the distance of the user.

The user detecting part 500 may determine the distance of the user in real-time. The focal length of the lens part 200 and the intensity of the image of the display panel 100 may be adjusted in real-time.

According to the present example embodiment, in the therapy mode, the display apparatus focuses the image of the display panel 100 having the skin therapy effect toward the user's face using the lens part 200. Thus, when the user ordinarily uses the display apparatus to watch television, to communicate with others, or to use an internet service, the display apparatus provides the skin care effect and the skin therapy effect to the user.

In addition, the lens part 200 and the image are adjusted based on the distance of the user from the display panel 100 so that the skin care effect and the skin therapy effect may be further improved.

Figure 7:
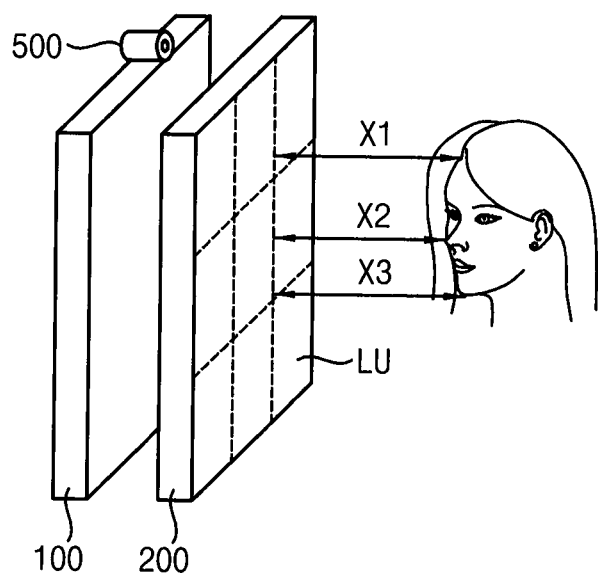
FIG. 7 is a perspective view illustrating a display apparatus according to an example embodiment.

FIG. 7 is a perspective view illustrating a display apparatus according to an example embodiment.

A display apparatus according to the present example embodiment is substantially the same as the display apparatus of the previous example embodiment explained referring to FIGS. 1 to 4 except that the display apparatus further includes a user detecting part, and the lens part includes a plurality of lens units LU. Thus, the same reference numerals will be used to refer to the same or like parts as those described in the previous example embodiment of FIGS. 1 to 4 and any repetitive explanation concerning the above elements will be omitted.

Referring to FIGS. 1 to 4 and 7, the display apparatus includes a display panel 100, a lens part 200 and the user detecting part 500.

The display panel 100 displays an image based on input image data.

The lens part 200 is disposed on the display panel 100. In a display mode, the lens part 200 transmits the image of the display panel 100 without refraction. In a therapy mode, the lens part 200 focuses the image of the display panel 100 toward a user's face.

The lens part 200 includes a plurality of lens units LU. The lens units LU may be independently driven. The lens units LU that form lens part 200 may be disposed in a matrix form.

The user detecting part 500 determines respective distances of different portions of a human face, for instance, the user's face from the lens part 200. For example, the user detecting part 500 may include a camera. For example, the user detecting part 500 may include a proximity sensor. For example, the user detecting part 500 may be disposed on a bezel portion of the display panel 100.

A focal length of the lens part 200 may be adjusted based on the distance of the portion of the user's face from lens panel 200. When a distance of a brow of the user from the lens part 200 is X1, a distance of a nose of the user from the lens part is X2, and a distance of a chin of the user from the lens part 200 is X3, a focal length of a first lens unit of the lens part 200 may be adjusted based on distances X1, X2, and X3. A focal length of a first lens unit of lens part 200 may be adjusted to focus the image of the display panel 100 so that light from the image of the display panel 100 is directed to, and concentrated at, the distance X1 of the brow of the user. A focal length of a second lens unit of the lens part 200 may be adjusted to focus the image of the display panel 100 so that light from the image of the display panel 100 is directed to, and concentrated at, the distance X2 of the nose of the user. A focal length of a third lens unit of the lens part 200 may be adjusted to focus the image of the display panel 100 so that light from the image of the display panel 100 is directed to, and concentrated at, the distance X3 of the chin of the user.

For example, the user detecting part 500 transmits the distances of the portions of user's face from the lens part 200 to the therapy controlling part 322 of the timing controller 320. The therapy controlling part 322 outputs the different lens control signals to the lens driver 400 based on the distances of the portions of user's face. The lens driver 400 drives the lens units LU of the lens part 200 to focus the image of the display panel 100 so that light from the image of the display panel 100 is directed onto, and concentrated on, the portions of the user's face at the measured distances.

The user detecting part 500 may determine the distances of the portions of the user's face in real-time. The focal length of the lens part 200 may be adjusted in real-time.

According to the present example embodiment, in the therapy mode, the display apparatus focuses the image of the display panel 100 so that light from the image of the display panel 100 having the skin therapy effect is directed toward, and concentrated on, the user's face using the lens part 200. Thus, when the user ordinarily uses the display apparatus to watch television, to communicate with others, or to use an internet service, the display apparatus provides the skin care effect and the skin therapy effect to the user.

In addition, the lens part 200 is adjusted based on the distances of the portions of the user's face so that the skin care effect and the skin therapy effect may be further improved.

Figure 8:
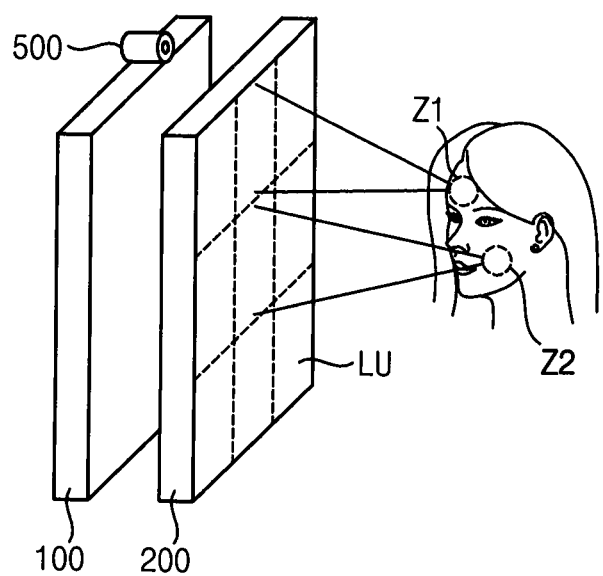
FIG. 8 is a perspective view illustrating a display apparatus according to an example embodiment.

FIG. 8 is a perspective view illustrating a display apparatus according to an example embodiment.

A display apparatus according to the present example embodiment is substantially the same as the display apparatus of the previous example embodiment explained referring to FIGS. 1 to 4 except that the display apparatus further includes a user detecting part, and the lens part includes a plurality of lens units LU. Thus, the same reference numerals will be used to refer to the same or like parts as those described in the previous example embodiment of FIGS. 1 to 4 and any repetitive explanation concerning the above elements will be omitted.

Referring to FIGS. 1 to 4 and 8, the display apparatus includes a display panel 100, a lens part 200 and the user detecting part 500.

The display panel 100 displays an image based on input image data.

The lens part 200 is disposed on the display panel 100. In a display mode, the lens part 200 transmits the image of the display panel 100 without refraction. In a therapy mode, the lens part 200 focuses the image of the display panel 100 toward a user's face.

The lens part 200 includes a plurality of lens units LU. The lens units LU may be independently driven. The lens units LU that form lens part 200 may be disposed in a matrix form.

The user detecting part 500 determines a skin condition of, for example, a human face, for instance, the user. For example, the user detecting part 500 may include a camera. For example, the user detecting part 500 may include a proximity sensor. For example, the user detecting part 500 may be disposed on a bezel portion of the display panel 100.

The lens units LU of the lens part 200 focus lights having different wavelengths that are selected based on the skin condition of the user. For example, a first lens unit of the lens part 200 may concentrate light having a first wavelength to a first zone Z1 in the user's face based on an identified skin condition of the first zone Z1. For example, a second lens unit of the lens part 200 may focus light having a second wavelength to a second zone Z2 in the user's face based on an identified skin condition of the first zone Z2. For example, the first lens unit may focus light having a wavelength representing green (e.g. about 550 nm) or red (e.g. about 633 nm), which has anti-wrinkle effect, to a brow area Z1 of the user which often becomes wrinkled. For example, the second lens unit may focus light having a wavelength representing green (e.g. about 415 nm), which has acne removal effect, to a cheek area Z2 of the user which is an area that often has acne.

For example, the user detecting part 500 transmits the identified skin condition of the user to the therapy controlling part 322 of the timing controller 320. The therapy controlling part 322 outputs the different lens control signals to the lens driver 400 based on to the skin condition of the user. The lens driver 400 drives the lens units LU of the lens part 200 to focus light having different wavelengths to the different portions of the user's face according to the skin condition of the different portions of the user's face.

The user detecting part 500 may determine the skin condition of the user in real-time. The wavelength of the light and a position at which the light is focused may be adjusted in real-time.

According to the present example embodiment, in the therapy mode, the display apparatus focuses the image of the display panel 100 having the skin therapy effect toward the user's face using the lens part 200. Thus, when the user ordinarily uses the display apparatus to watch television, to communicate with others, or to use an internet service, the display apparatus provides the skin care effect and the skin therapy effect to the user.

In addition, the lens part 200 is adjusted based on the identified skin condition of the user so that the skin care effect and the skin therapy effect may be further improved.

Figure 9:
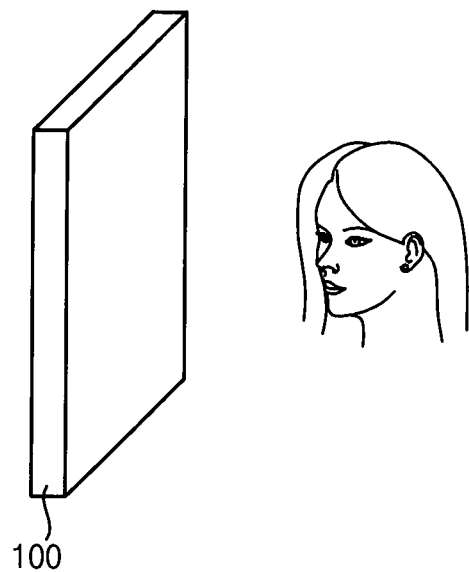
FIG. 9 is a perspective view illustrating a display apparatus according to an example embodiment.
Figure 10A:
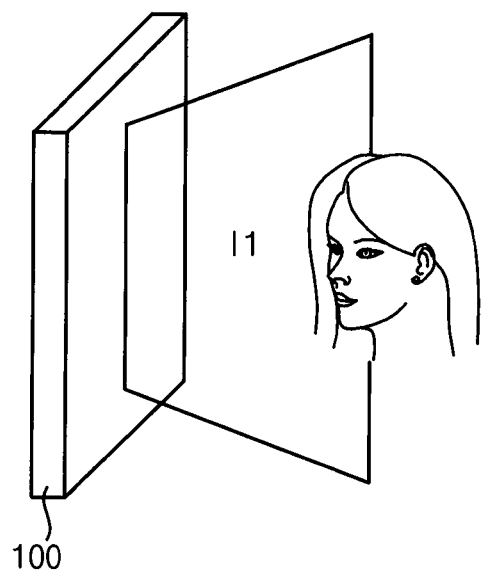
FIG. 10A is a perspective view illustrating an image displayed by the display apparatus of FIG. 9 in a display mode.
Figure 10B:
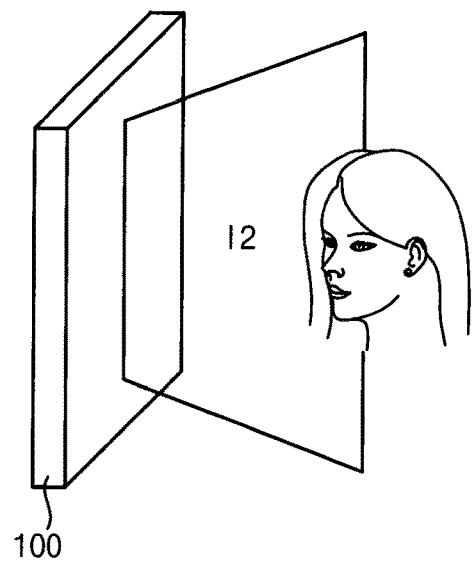
FIG. 10B is a perspective view illustrating an image displayed by the display apparatus of FIG. 9 in a therapy mode.

FIG. 9 is a perspective view illustrating a display apparatus according to an example embodiment. FIG. 10A is a perspective view illustrating an image displayed by the display apparatus of FIG. 9 in a display mode. FIG. 10B is a perspective view illustrating an image displayed by the display apparatus of FIG. 9 in a therapy mode.

A display apparatus according to the present example embodiment is substantially the same as the display apparatus of the previous example embodiment explained referring to FIGS. 1 to 4 except that the display apparatus does not include the lens part and the display panel displays different images depending upon the mode signal. Thus, the same reference numerals will be used to refer to the same or like parts as those described in the previous example embodiment of FIGS. 1 to 4 and any repetitive explanation concerning the above elements will be omitted.

Referring to FIGS. 3, 4, 9, 10A and 10B, the display apparatus includes a display panel 100.

The display panel 100 displays a first image I1 based on an input image data in a display mode. The display panel 100 displays a second image I2 which has a therapy wavelength in a therapy mode.

The first image I1 may be a general display image. The first image I1 may not have the therapy wavelength.

The second image I2 may be a therapy image having the therapy wavelength. The therapy wavelength may be, for example, one of about 415 nm representing blue, about 550 nm representing green and about 633 nm representing red. The therapy image may be a single color image irrelevant to, i.e., not based on, the input image data. The single color image may be, for example, a red image, a green image and a blue image. The therapy image may be a mixed color image of at least two of the red image, the green image and the blue image.

Alternatively, the therapy image may be a display image generated based on the input image data.

According to the present example embodiment, in the therapy mode, the display apparatus displays the therapy image having the therapy effect. Thus, when the user uses the display apparatus, the display apparatus provides the skin care effect and the skin therapy effect to the user.

Figure 11:
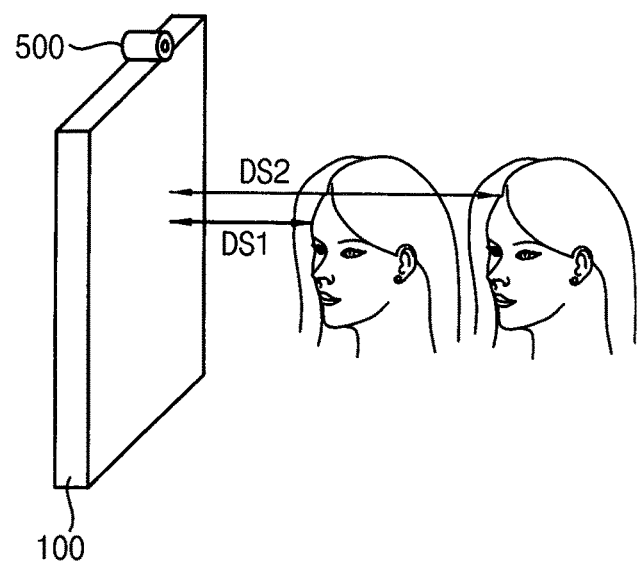
FIG. 11 is a perspective view illustrating a display apparatus according to an example embodiment.

FIG. 11 is a perspective view illustrating a display apparatus according to an example embodiment.

A display apparatus according to the present example embodiment is substantially the same as the display apparatus of the previous example embodiment explained referring to FIGS. 9 to 10B except that the display apparatus further include a user detecting part. Thus, the same reference numerals will be used to refer to the same or like parts as those described in the previous example embodiment of FIGS. 9 to 10B and any repetitive explanation concerning the above elements will be omitted.

Referring to FIGS. 3, 4, 9 to 11, the display apparatus includes a display panel 100 and the user detecting part 500.

In a display mode, the display panel 100 displays a first image I1 based on an input image data. In a therapy mode, the display panel 100 displays a second image I2 having a therapy wavelength.

The user detecting part 500 determines a distance of the user from the display panel 100. For example, the user detecting part 500 may include a camera. For example, the user detecting part 500 may include a proximity sensor. For example, the user detecting part 500 may be disposed on a bezel portion of the display panel 100.

Intensity of the second image I2 having the therapy effect may be adjusted based on the distance of the user from the display panel 100. When the user is relatively close to the display panel 100, the intensity of the second image I2 of the display panel 100 may be weakened. When the user is relatively far from the display panel 100, the intensity of the second image I2 of the display panel 100 may be strengthened.

For example, the user detecting part 500 transmits the distance of the user to the therapy controlling part 322 of the timing controller 320. The therapy controlling part 322 adjusts the intensity of the second image I2 of the display panel 100 based on the distance of the user from the display panel 100.

For example, the therapy controlling part 322 may manage a wavelength of the image of the display panel 100, the duration of the therapy, and the intensity of the image of the display panel 100 according to the distance of the user. The wavelength of the image of the display panel 100 and the duration of the therapy may be fixed values. The intensity of the image of the display panel 100 may be a variable that depends on the distance of the user from the display panel 100.

The therapy controlling part 322 may compare the skin condition of the user before therapy and the skin condition of the user after therapy using the user detecting part 500 and provide the results of the comparison to the display panel 100.

The user detecting part 500 may determine the distance of the user from the display panel 100 in real-time. The intensity of the second image I2 of the display panel 100 may be adjusted in real-time.

According to the present example embodiment, in the therapy mode, the display apparatus displays the therapy image having the therapy effect. Thus, when the user uses the display apparatus, the display apparatus provides the skin care effect and the skin therapy effect to the user.

In addition, the intensity of the therapy image is adjusted based on the distance of the user from the display panel 100 so that the skin care effect and the skin therapy effect may be further improved.

Figure 12:
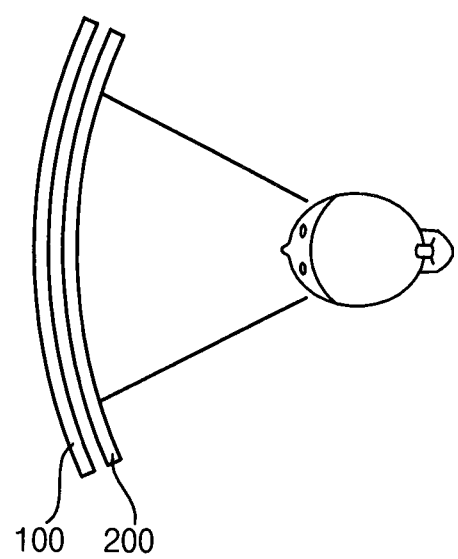
FIG. 12 is a perspective view illustrating a display apparatus according to an example embodiment.

FIG. 12 is a perspective view illustrating a display apparatus according to an example embodiment.

A display apparatus according to the present example embodiment is substantially the same as the display apparatus of the previous example embodiment explained referring to FIGS. 1 to 4 except that the display panel and the lens part are curved. Thus, the same reference numerals will be used to refer to the same or like parts as those described in the previous example embodiment of FIGS. 1 to 4 and any repetitive explanation concerning the above elements will be omitted.

Referring to FIGS. 1 to 4 and 12, the display apparatus includes a display panel 100 and a lens part 200.

The display panel 100 displays an image based on input image data.

The display panel 100 has a curved shape. The display panel 100 may be fixed in the curved shape. Alternatively, the display panel 100 may be a flexible display panel which it is possible to bend into the curved shape.

The lens part 200 is disposed on the display panel 100. In a display mode, the lens part 200 transmits the image of the display panel 100 without refraction. In a therapy mode, the lens part 200 concentrates the image of the display panel 100 toward a user's face.

The lens part 200 has a curved shape corresponding to the shape of the display panel 100. The lens part 200 may be fixed in the curved shape. Alternatively, the lens part 200 may be a flexible lens panel which it is possible to bend into the curved shape.

For example, distances from several portions of the lens part 200 to the user may be uniform.

According to the present example embodiment, in the therapy mode, the display apparatus focuses the image of the display panel 100 having the skin therapy effect toward the user's face using the lens part 200. Thus, when the user ordinarily uses the display apparatus to watch television, to communicate with others, or to use an internet service, the display apparatus provides the skin care effect and the skin therapy effect to the user.

In addition, the efficiency of the concentration of light may be improved by the curved display panel 100 and the curved lens part 200 so that the skin care effect and the skin therapy effect may be further improved.

As explained above, according to the display apparatus of the present example embodiments, in a therapy mode, an image is focused toward a user's face or a therapy image is displayed on a display panel. Thus, the display apparatus may provide the skin care effect and the skin therapy effect.

The foregoing is illustrative of the present disclosure and is not to be construed as limiting thereof. Although a few example embodiments have been described, those skilled in the art will readily appreciate that many modifications are possible in the example embodiments without materially departing from the novel teachings and advantages of the present disclosure. Accordingly, all such modifications are intended to be included within the scope of the present disclosure, including the claims. In the claims, means-plus-function clauses are intended to cover the structures described herein as performing the recited function and not only structural equivalents but also equivalent structures. Therefore, it is to be understood that the foregoing is illustrative and is not to be construed as limited to the specific example embodiments disclosed, and that modifications to the disclosed example embodiments, as well as other embodiments, are intended to be included within the scope of the disclosure, including the appended claims.

What is claimed is:

1. A display apparatus for providing light therapy to skin, the display apparatus comprising:
   a display panel configured to display an image based on input image data;
   a lens driver;
   a lens disposed in front of the display panel and responsive to signals from the lens driver;
   a camera configured to determine a position, relative to the lens, of a face in front of the display panel;
   wherein the display apparatus is configured to switch the display panel from a display mode to a skin therapy mode, wherein the skin therapy mode includes adjustment of at least one of color coordinates, light intensity or duration of the displayed image based on the position of the face, for providing the light therapy to skin of the face; and
   wherein the display apparatus is configured to control the lens to operate in the display mode and transmit the image without refraction to a display region, and to operate in the light therapy mode and focus the image to a particular region of the display region that includes the position of the face, wherein the particular region is smaller than the display region, the display region and the particular region are on a first side of the lens and the display panel is on a second side of the lens that is opposite the first side, and the particular region and the display region overlap and are at a same distance from the lens.

2. The display apparatus of claim 1, wherein the display panel uses a first color coordinate in the first mode and a second color coordinate in the second mode, wherein each color coordinate defines wavelength ranges used for blue light, green light, and red light.

3. The display apparatus of claim 2, wherein a wavelength of blue light is 415 nm in the second color coordinate, a wavelength of green light is 550 nm in the second color coordinate and a wavelength of red light is 633 nm in the second color coordinate.

4. The display apparatus of claim 1, further comprising a proximity sensor configured to determine a position of an object relative to the lens.

5. The display apparatus of claim 4, wherein the lens part, in operation, adjusts a position of the particular region according to the position of the face.

6. The display apparatus of claim 1, wherein the lens comprises a liquid crystal lens.

7. The display apparatus of claim 1, further comprising a first part and a second part,
   wherein the first part operates to receive the input image data and output a first image data to the second part in a display the first mode and a second image data to the second part in the therapy second mode, and
   wherein the second part operates to compensate a grayscale of each of the first and second image data and rearranges the first and second image data to generate first and second data signals DATA1 and DATA2 for a data driver.

8. The display apparatus of claim 1, wherein the display panel is configured to display, in the skin therapy mode, light of wavelength between 385 to 415 nm for blue light, 520 to 580 nm for green light, and 603 to 663 nm for red light.

* * * * *